(12) United States Patent
Harding

(10) Patent No.: US 6,693,988 B2
(45) Date of Patent: Feb. 17, 2004

(54) ARRANGEMENT FOR MEASURING THE PULSE TRANSMISSION SPECTRUM OF X-RAY QUANTA ELASTICALLY SCATTERED IN A SCANNING AREA FOR CONTAINERS

(75) Inventor: Geoffrey Harding, Hamburg (DE)

(73) Assignee: Yxlon International X-Ray GmbH, Hamburg (DE)

( * ) Notice: Subject to any disclaimer, the term of this patent is extended or adjusted under 35 U.S.C. 154(b) by 0 days.

(21) Appl. No.: 10/099,866

(22) Filed: Mar. 14, 2002

(65) Prior Publication Data

US 2003/0031295 A1 Feb. 13, 2003

(30) Foreign Application Priority Data

Mar. 14, 2001 (EP) .......................................... 01106227

(51) Int. Cl.⁷ .......................................... G01N 23/201
(52) U.S. Cl. ........................... 378/86; 378/70; 378/90; 378/57
(58) Field of Search ............................ 378/86, 87, 88, 378/89, 90, 70, 7, 57, 4, 20, 145, 146, 147

(56) References Cited

U.S. PATENT DOCUMENTS

| | | | |
|---|---|---|---|
| 5,008,911 A | * | 4/1991 | Harding .................. 378/86 |
| 5,265,144 A | | 11/1993 | Harding et al. |
| 5,394,453 A | | 2/1995 | Harding |
| 5,600,303 A | | 2/1997 | Husseiny et al. |
| 5,602,893 A | | 2/1997 | Harding |
| 6,054,712 A | * | 4/2000 | Komardin et al. ..... 250/363.06 |

\* cited by examiner

*Primary Examiner*—Edward J. Glick
*Assistant Examiner*—Hoon Koo Song
(74) *Attorney, Agent, or Firm*—Friedrich Kueffner

(57) ABSTRACT

A baggage inspection device based on coherent x-ray scatter has an x-ray source on one side of the scanning area and detectors on the other side of the scanning area. The detectors measure the energy of the scattered x-ray quanta. A primary ray collimator is arranged between scanning area and x-ray source. A secondary ray collimator for scattered rays is arranged between scanning area and detectors. The detectors are positioned on a Z axis forming an axis of symmetry for the secondary ray collimator. A point 0 on the Z axis forms the origin of a Cartesian coordinate system. The primary ray collimator allows passage only of x-ray beams impinging on the point 0. The x-ray source has an extended anode with a focus position controlled electronically about the anode length. Primary ray collimator and x-ray source extend cylindrically symmetrically about the symmetry axis or parallel to the Y axis in the X-Y plane.

15 Claims, 2 Drawing Sheets

ARRANGEMENT FOR MEASURING THE PULSE TRANSMISSION SPECTRUM OF X-RAY QUANTA ELASTICALLY SCATTERED IN A SCANNING AREA FOR CONTAINERS

BACKGROUND OF THE INVENTION

1. Field of the Invention

The invention relates to an arrangement for measuring the pulse transmission spectrum of x-ray quanta elastically scattered in a scanning area for containers, comprising a polychromatic x-ray source arranged on one side of the scanning area and a detector arrangement arranged on the other side of the scanning area for measuring the energy of the scattered x-ray quanta as well as a primary ray collimator arrangement and a secondary ray collimator arrangement, allowing passage only of scattered rays within a certain scatter angle range to the detector arrangement, wherein the primary ray collimator arrangement is arranged between the scanning area and the x-ray source and the secondary ray collimator arrangement is arranged between the scanning area and the detector arrangement, and further comprising means for processing the measured signals.

2. Description of the Related Art

Such an arrangement is known, for example, from European patent document EP-B1-360 347.

Moreover, baggage inspection systems are known which operate on the principle of examining with coherent x-rays (coherent x-ray scanning, CXRS), for example, disclosed in European patent document EP-A1-0 556 887. The devices of these systems are based on an arrangement of radiation source and detector in which the primary ray is fixed relative to the other components. In order to be able to analyze a container, such as a piece of baggage or the like, and its contents completely, the entire measuring system must be moved relative to the corresponding part to be examined. The corresponding mechanism is often slow, clumsy, and complicated so that scanning times of 60 seconds are common.

Moreover, the measuring time depends on the power of the x-ray source. In order to provide safe information in regard to the presence of explosives, drugs and the like within the piece of baggage, it is necessary that a certain number of scattered quanta are detected. The higher the power of the x-ray tube, the shorter the required measuring time. The maximum continuous power of a rotary anode tube is approximately 10 kW. This value, in addition to the mechanism, presents a limitation for the minimal scanning time of the piece of baggage which is approximately 1 minute.

The output signals of the detector elements can be processed such as, in particular, disclosed in the German patent application P 41 01 544. This known processing method is therefore not to be explained in detail in this context. It shall only be mentioned that for each detector element one processing channel is provided in which the signal is amplified, digitalized, and supplied to a pulse height analyzer which registers the number of x-ray quanta in the different energy ranges. For each detector element and for each energy range this number is divided by the number of x-ray quanta which have been registered by means of the central detector $D_0$ for the corresponding energy range. This provides the respective energy spectrum for each detector element, independent of the energy distribution of the x-ray quanta emitted by the x-ray source and substantially independent of the weakening of the scattered radiation caused by the object.

X-ray tubes with "jump focus" (the focus can jump back and forth, i.e., is deflected) are known in the prior art and are commonly referred to as swept focus or scanning focus; an example is Digi-Ray® in which the "inverse geometry" is preferred. This type of arrangement is called "inverse" because the traditional functions of x-ray source and detector (i.e., of point detector and extended source) is reversed in this system. The reference Solomom E. G., Wilfly B. P., Van Lysel M. S., Joseph A. W., and Heanue J. A., 1999, *Scanning beam digital x-ray (SBDX) system for cardiac angiography*, Physics of Medical Imaging SPIE Proc. 3659, 246–257 (Eds. J. M. Boone and J. T. Dobbins) relates to a publication of the company Cardiac Mariners Inc. This company uses an x-ray source with "jump focus" for generating blood vessel images, primarily of the heart. Since x-ray sources with scanning beams or "jump focus" are disclosed sufficiently in scientific and technical literature with respect to "inverse geometry", they will not be discussed in detail in this context.

SUMMARY OF THE INVENTION

It is an object of the present invention to improve the arrangement of the aforementioned kind such that essentially no mechanical movement of the x-ray source is required and, at the same time, an amplification of the power of the x-ray beams is achieved so that a substantial shortening of the scanning or examination duration of the containers within the range of seconds is possible, in particular, for use in airports.

In accordance with the present invention, this is achieved in that the detector arrangement $(D_1, \ldots D_n)$ is positioned on a Z axis, which simultaneously forms an axis of symmetry about which the secondary ray collimator arrangement extends cylindrically symmetrically, wherein on the Z axis a point 0 is provided which determines the origin of a Cartesian coordinate system with X axis and Y axis, wherein the conveying axis for the container to be examined extends parallel to the Z axis, and in that the primary ray collimator arrangement (P) allows passage only of x-ray beams which are substantially impinging on the point 0, wherein the x-ray source (Q) is arranged behind the primary ray collimator arrangement (P) with an extended anode whose focus position can be electronically controlled about the length of the anode, and wherein the primary ray collimator arrangement (P) and the x-ray source (Q) extend cylindrically symmetrically about the axis of symmetry or linearly parallel to the Y axis in the X-Y plane.

In the CXRS arrangement or device according to the invention, the axis of symmetry, in contrast to all CXRS systems presently known, does not extend through the focus of the x-ray tube or x-ray source. Accordingly, the present invention describes a novel CXRS geometry based on an x-ray tube with "jump focus" (swept focus) which is characterized particularly in that mechanical scanning movements—aside from the required forward movement on a conveyor belt—when examining containers of any kind, in particular, pieces of luggage and the like, are avoided and an x-ray source with great power can be used. Moreover, it is possible to significantly reduce the surface and thus the technical complexity of the detector arrangement which in the known systems represents an important cost factor. Cooling by using the Peltier effect is possible according to the invention so that the use of liquid nitrogen or complex cryogenic generators, as needed in the case of semiconductor detectors, can be avoided.

For a better understanding of the invention, the invention will be explained in the following with the aid of an embodiment. The values in regard to dimensions are given in mm and all angles are given in radian. The invention is not limited to the illustrated and described embodiment but can be adapted within the gist of the present invention.

Table 1 provides exemplary geometric parameters for the main components of the inventive CXRS arrangement with "jump focus" (swept focus); and Table 2 illustrates values for the coordinates of the detector elements, the slits and the radius of the imaging slit at the point 0.

DESCRIPTION OF THE PREFERRED EMBODIMENTS

As a result of the annular symmetry it is beneficial to identify the positions of the main components by providing their radius relative to 0. Accordingly, for $R_s$ (the initial radius relative to 0) a value of 2150 mm is assumed, and so on. On the other hand, it is recommended to employ a rectangular Cartesian coordinate system based on the fact that the pieces of baggage are transported on a conveyor belt. Accordingly, $L_s$ (=400 mm) is the distance from the x-ray source to the upper side of the baggage tunnel in the Z direction, $L_0$ (=650 mm) is the height of the baggage tunnel, and $L_d$ (=1100 mm) is the spacing between the conveyor belt and the Z-Y plane and the Z direction.

Figure 1:
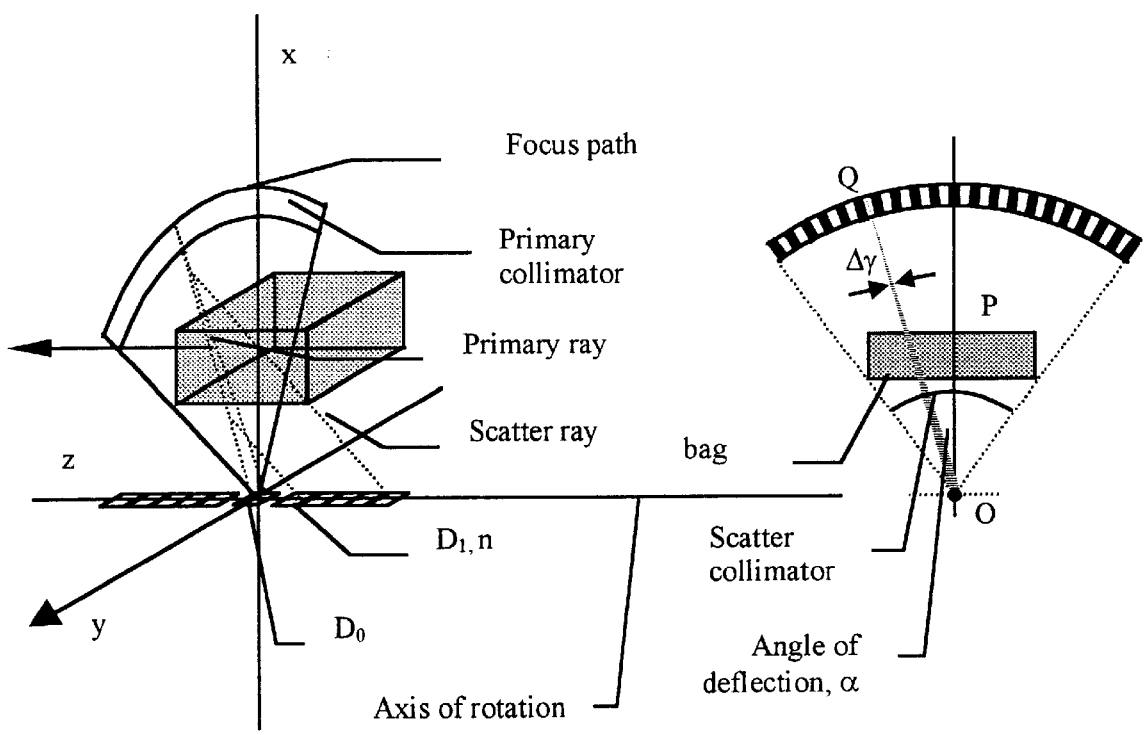
FIG. 1 shows on the left side a perspective illustration of the CXRS arrangement according to the invention and on the right side a view along the axis of symmetry.

On the left side of FIG. 1, the Z axis defines a cylindrically symmetric geometry. The main component of the system, i.e., the x-ray source, the primary collimator, and the scatter collimator are arranged annularly, at least in approximation, with symmetry of revolution about the Z axis. The piece of luggage to be inspected is transported parallel to the Z axis on a belt (not illustrated).

A point 0 is defined which is on the Z axis and which is the point of origin of the Cartesian coordinate system with X axis and Y axis. The area within the X-Y plane is the area of baggage radiography imaging. At a radius $R_s$ from point 0 an x-ray source of "jump focus" (swept focus) is provided in the radiography imaging plane. It is configured to allow the x-ray focus to be deflected about a circular arc having a rotational center at 0. In the arrangement according to the invention, the maximum deflection angle is ±20° within the X-Y plane.

FIG. 1 shows in dashed lines a primary ray which, emitted from the focal point Q, impinges on the detector $D_0$. Two further rays (dashed lines) are shown which are scattered by the upper and lower side of the piece of baggage (hatched). Because of the scattered ray collimator, these rays impinge only on the detector elements $D_1$ and $D_n$. The scattered ray collimator connects scatter points in the object space with a certain radius, R, from the Z axis with a corresponding detector element, I, independent of the position, Q, of the x-ray source. The scattered ray collimator ensures also that the scatter angle remains independent of the index, I.

The geometry of the CXRS arrangement with "jump focus" (swept focus) can be seen better on the right side of FIG. 1 which illustrates an X-Y cross-section of the system. When the electron beam coming from the x-ray tube is deflected along the anode, this results in a movable x-ray source. At a certain point Q the x-rays are emitted into the entire space. Because of symmetry, the following is apparent: When the primary collimator and the scatter collimator are configured to extend cylindrically symmetrically about the Z axis, the scatter angle does not depend on the position of Q. Precisely, it would be possible to activate the entire anode arc and to simultaneously radiate the piece of baggage from many different directions. The most important disadvantage of this operational mode is that the coherent scatter of small pieces to be examined, for example, plastic explosives, would be superimposed by the scatter of all other materials within the piece of luggage which can reflect rays onto the detector element and are positioned within the arc of the primary ray (partial voxel problem). On the other hand, it is possible to activate only a single point on the anode (with variable position). The result would be a scatter signal with a high spatial resolution but a reduced intensity. In general, it is recommended to select a focus length (along the arc) which corresponds to the dimensions of the smallest object which is to be detected. Based on experience with already developed baggage inspection systems which employ the CXRS method, a focal length of approximately 50 mm (defined by the angle range $\delta\alpha$) which corresponds in the piece of baggage to a "footprint" of approximately 30 mm is a good compromise. In this connection, the position (defined by the angle $\alpha$) of the anode of the 50 mm focus is, of course, variable over the course of time. The focal width in the Z direction depends on the desired resolution in the pulse transmission spectrum and is conventionally 0.2 mm.

As described above, the position of the focal spot, illustrated by the angle $\alpha$ in FIG. 1, can be variable over time. When the electron beam of the x-ray tube is deflected along the anode, this results in a movable x-ray source. The focus has a length of, for example, 50 mm. In the interest of maintaining the symmetry of revolution, a primary ray collimator is however positioned between the "jump focus" x-ray source (swept focus x-ray source) and the piece of luggage. In this way, all those rays are absorbed which are outside of a small fan with the opening angle $\Delta\gamma$. In practice, such a collimator, as illustrated in FIG. 1, is realized by lamellas with regular spacing (Soller slit) wherein they are comprised of a material which absorbs x-rays relatively strongly. When the lamellas have a length of 250 mm, the spacing between neighboring lamellas is approximately 1 mm. The corresponding value of the opening angle, $\Delta\gamma$, is 0.4°.

In the vertical direction, i.e., parallel to the Z axis, the primary ray opening for a distance of 250 mm from the source should have a width of 0.2 mm.

The secondary (coherent) radiation induced in the object is recorded by a linear array of energy-resolving detectors $D_1, D_i \ldots D_n$. They can be comprised of germanium or room temperature semiconductors (for example, cadmium-zinc-telluride—CdZnTE) and are within the Y-Z plane on the Z axis. Since the measurement of the weakening of the primary ray in the piece of luggage provides useful information, a detector $D_0$ is provided at the point 0 and records the transmitted radiation. This information can be used for attenuation corrections. Unfortunately, the x-ray focus of 50 mm length is too great for obtaining a high-resolution radiographic image of the piece of luggage.

Figure 3:
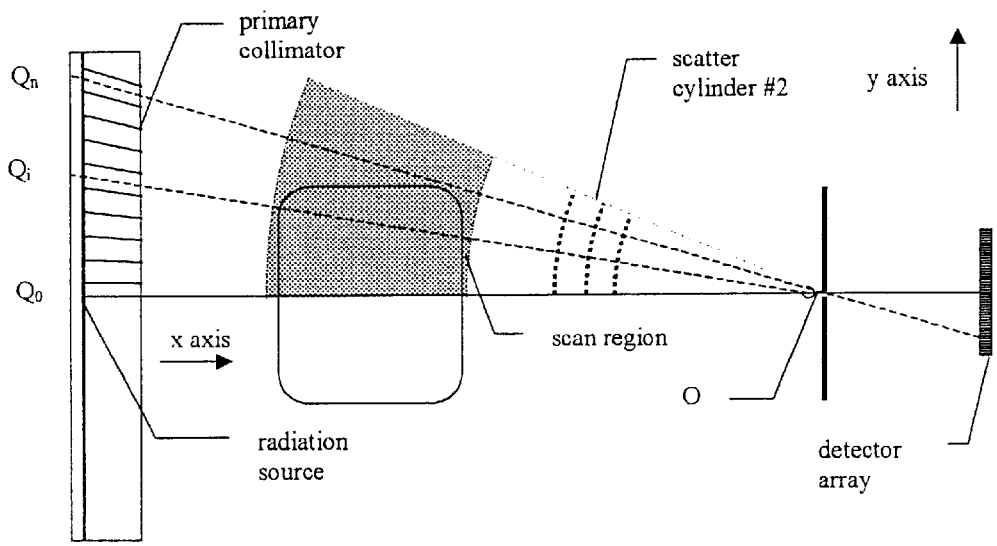
FIG. 3 is an illustration of a further CXRS arrangement with linear detector array for obtaining radiograph images.

According to an advantageous further embodiment of the invention (FIG. 3) at the point 0 an aperture of a width in the Z direction of between 0.02 mm and 0.2 mm is provided.

Behind the aperture a linear array of detectors is provided (FIG. 3) which detects the transmitted radiation in such a way that a projection image (radiographic image) of the piece of luggage results on the linear array of detectors.

When assuming a radiation scatter angle θ of 0.0376 and, moreover, the object area of the height $L_0$ with parallel extending scattered rays is projected onto the detector, the entire width of the detector in the Z direction can be easily determined according to the following equation:

$$D_z = L_0 \sin(\theta)$$

A representative value for $L_0$ is 650 mm (see below). Accordingly, $D_z$ then is =24.4 mm. Similar to the first detector element, $D_1$ is staggered by $L_d \sin(\theta)$ from the X-Y plane and is thus removed 41.36 mm from the point 0. A typical detector element width in the Z direction is 50. $\sin(\theta)=1.8$ mm for a 50 mm resolution in the object space. Moreover, it can be seen that at least 14 detector elements (=24.4 mm/1.8 mm) are required.

The detector elements show the primary ray bundle passing through one or several annular slits. There is a definite relationship between the detector element index i and the radius from the point 0 of the illustrated primary ray arc. Moreover, the use of a plurality of slits is possible, as described in different CXRS patents, in order to ensure that the scatter angle θ is practically constant independent of the detector element. Independent of the source deflection angle α, the detector elements $D_1, D_i \ldots D_n$ always recognize the scattered rays which are scattered outside of the X-Y plane at a constant angle θ. This condition is achieved in that the scatter collimator is arranged annularly symmetric about the Z axis.

For a value $L_d$ of 1100 mm favorable image features (object on detector ray field) are ensured because then the following holds true: $L_d \gg L_0$. Moreover, with this relatively great value for $L_d$, the scatter slit collimator is easily fitted into the available surface.

With respect to the geometric requirements for the inventive CXRS system with "jump focus", different dimensions are suggested, as listed in Table 1. These dimensions are justified primarily because they correspond to scatter angles of already realized systems and because a suitcase with a maximum width of 800 mm and a maximum height of 605 mm can be checked in one pass (from $-20° \leq \alpha \leq 20°$).

The width of a certain detector element (i.e., its expansion in the Z direction) effects also the scatter angle θ. This variation and the variations described in the following paragraphs have been calculated by using basic trigonometry. A detector width of approximately 1.8 mm is appropriate. This value corresponds with a voxel height in the suitcase of approximately 40 mm for a scatter angle of 0.0376 radian.

The scatter angle depends on the length of the detector element. The resolution condition is fulfilled by a detector length of 10 mm.

In order to be able to produce an image of an object surface of 650 mm on the detector (this is required for imaging a suitcase of a height of 605 mm), the entire expansion of the detector ray field in the Z direction must be 24.4 mm. The first element of the detector ray field, which is responsible for the image of the suitcase directly above the conveyor belt, is moved by 41.4 mm away-from the X-Y plane. A doubling of the scattered signal can be achieved in that on each side of the primary ray deflection plane a detector ray field is established. The complete width of these two detectors with a radiography imaging surface area in the Z direction is 125 mm.

As has been already described above, the scatter collimator must be realized by openings which extend annularly symmetrically about the Z axis.

Since 14 detector elements of a width of 1.8 mm are required in order to cover the entire object space, a scatter collimator is described here with a slit for each pair of detector elements. The detector elements have the index i ($1 \leq i \leq 14$) wherein i=1 is the element with the smallest spacing to the X-Y plane. Table 2 represents values for the Z coordinate of the detector elements, the slits and the radius of the imaging slit from the point 0.

Table 2 illustrates that the scatter collimator is comprised of only 3 cylinders. In order to be able to achieve the required resolution in the pulse transmission spectrum, the slits of the scatter collimator (by using the dimensions provided in Table 1) must be, on average, approximately 0.4 mm.

Based on the data for the radius of the x-ray source (0 =2100 mm) provided above and the maximum deflection angle (±20°), the anode must have a length of 1600 mm. Supposed that the primary collimator is comprised of lamellas which are aligned to the point 0, it is inconsequential whether the anode has the geometry of a circular arc or is linear.

Figure 2:
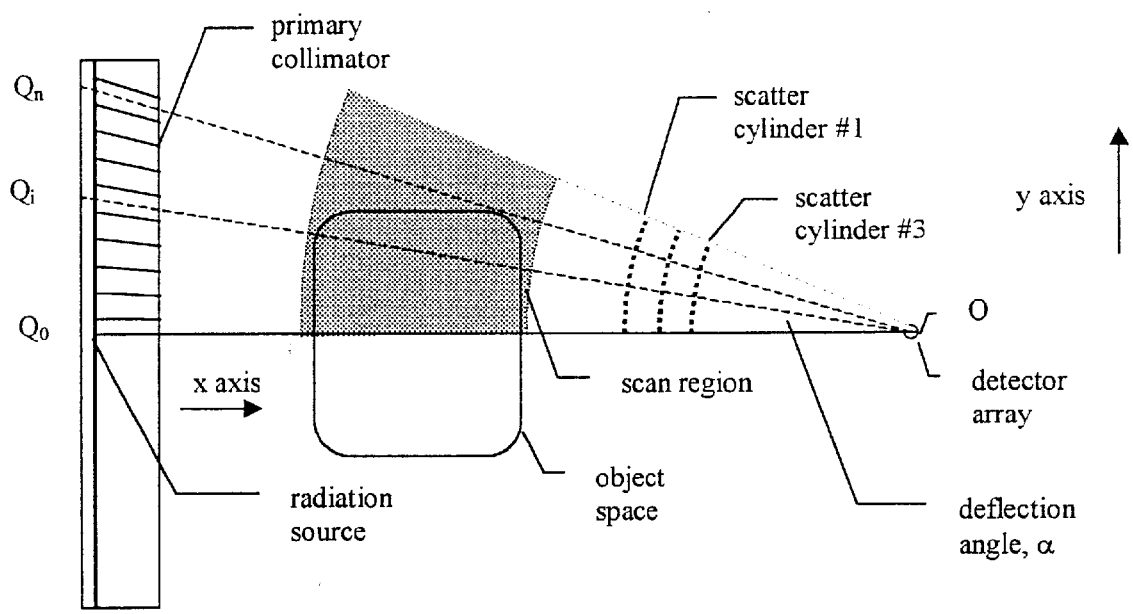
FIG. 2 is an illustration of a second CXRS arrangement according to the invention with linear x-ray tube.

Such an arrangement (only the half above the X axis is relevant) is illustrated in FIG. 2 at the top. The scatter collimator which is comprised of three cylindrical apertures, is illustrated in dashed lines in FIG. 2 because the slits are positioned outside of the section plane.

The linear x-ray tube with "jump focus" can be realized in a compact way when a plurality of cathodes are provided which are individually controlled. Each cathode generates an electron beam of approximately 50 mm length when it is switched active. Otherwise, the electron beam is suppressed by a grid voltage. By sequentially switching the cathodes, an x-ray source results on the positions $Q_0$, $Q_1$ etc. with a residence time which can be electronically controlled. The entire length of the anode in the Y direction is 1565 mm.

The scientific literature contains known equations (see in this connection A. Bouwers, An x-ray tube with a rotating anode, Physics, 10, 125 1930) which provide relations between the anode temperature, the power of the electron beam, and the residence time of the beam on the anode. As a result of these equations, it can be estimated that a focus with dimensions of 1 mm×50 mm for a load with 50 kW over a pulse time of 1000 μs results in a maximum anode temperature of 1200° C. In order for the introduced power not to melt the anode, it is required that the anode is comprised of a material with a high heat conductivity or with a high melting temperature. Tungsten and gold are especially suitable for this purpose. Moreover, it is necessary that the heat is dissipated quickly which can be achieved by an anode cooling with water, oil or the like.

When it is considered that a projected focus magnitude of approximately 200 μm is required, an anode angle of 11° is required in order to project a spot of a width of 200 μm when the electron beam has a "real" width of 1 mm.

It is required to provide 32 focus positions in order to perform inspections over the entire length of a tube anode of 1600 mm length with a focal spot of 50 mm length. For a residence time of 1 ms for each focus position, the scanning of a slice takes 32 ms for recording the data. As an alternative, the system can scan 30 slices per second. Since the CXRS configuration with "jump focus" is as efficient in regard to the production of scattered photons per kW tube power as the previously realized systems, this results in a total inspection duration of 6 s for each piece of luggage.

While specific embodiments of the invention have been shown and described in detail to illustrate the inventive principles, it will be understood that the invention may be embodied otherwise without departing from such principles.

TABLE 1

Geometrical parameters for major components of swept-focus CXRS

| Parameter | Value | Comment |
|---|---|---|
| $R_s$ | 2150 mm | Radius of focus from O |
| $R_o$ | 1750 mm | Radius of top of object space relative to O. |
| $R_T$ | 1100 mm | Radius of bottom of object space. |
| $L_s$ | 550 mm | Focus to top of tunnel separation |
| $L_o$ | 605 mm | Maximum suitcase height |
| $L_D$ | 1100 mm | Conveyor belt to detector separation |
| $\theta$ | 0.0376 | Mean angle of scatter |
| $\alpha_{max}$ | ±20° | Maximum deflection angle |
| $B_y$ | 800 mm | Bag width in Y direction |
| $B_x$ | 604 mm | Bag height in X direction |
| $F_z$ | 200 µm | Focus size in Z direction |
| $\delta\gamma$ | 0.4° | Angular range of fan |
| $Z_c$ | 41.4 mm | Displacement of detector front edge from scan slice |
| $D_z$ | 24.4 mm | Detector width |
| $D_Y$ | 10 mm | Detector length |

TABLE 2

| I | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| $Z_I$ | 42.7 | 44.5 | 46.2 | 48.0 | 49.8 | 51.5 | 53.3 | 55.0 | 56.8 | 58.6 | 60.4 | 62.1 | 63.9 | 65.6 |
| $Z_s$ | 20.9 | 20.9 | 24.4 | 24.4 | 24.4 | 24.4 | 28.0 | 28.0 | 27.1 | 27.1 | 30.6 | 30.6 | 34.1 | 34.1 |
| $R_I$ | 546 | 546 | 546 | 546 | 639 | 639 | 639 | 639 | 755 | 755 | 755 | 755 | 755 | 755 |

What is claimed is:

1. An arrangement for measuring the pulse transmission spectrum of x-ray quanta elastically scattered in a scanning area for containers, the arrangement comprising:

a scanning area;

a polychromatic x-ray source arranged on one side of the scanning area;

a detector arrangement arranged on the other side of the scanning area, wherein the detector arrangement measures the energy of the scattered x-ray quanta;

a primary ray collimator arrangement arranged between the scanning area and the x-ray source;

a secondary ray collimator arrangement, allowing passage only of scattered rays within a certain scatter angle range to the detector arrangement, arranged between the scanning area and the detector arrangement;

means for processing the measured signals;

wherein the detector arrangement is positioned on a Z axis, which simultaneously forms an axis of symmetry about which the secondary ray collimator arrangement extends cylindrically symmetrically;

wherein on the Z axis a point 0 is provided which determines the origin of a Cartesian coordinate system with X axis and Y axis;

wherein a conveying axis for a container to be examined extends parallel to the Z axis;

wherein the primary ray collimator arrangement allows passage only of x-ray beams which are substantially impinging on the point 0;

wherein the x-ray source is arranged behind the primary ray collimator arrangement together with an extended anode having a focus position controlled electronically about the length of the anode; and wherein the primary ray collimator arrangement and the x-ray source extend cylindrically symmetrically about the axis of symmetry or linearly parallel to the Y axis in the X-Y plane.

2. The arrangement according to claim 1, wherein the detector arrangement is comprised of detector elements which detect the scattered radiation resulting in the scanning area, wherein two detector arrangements with detector elements are arranged mirror-symmetrically about the point 0, wherein each of the two detector arrangements has at least 10 up to a maximum of 50 detector elements, wherein the detector elements are comprised of semiconductor material.

3. The arrangement according to claim 2, wherein the semiconductor material is germanium or CdZnTe.

4. The arrangement according to claim 2, wherein on the point 0 either a detector for measuring the transmitted radiation or an aperture is positioned through which the transmitted radiation passes and is registered on a linear array of detectors sensitive to x-ray radiation, wherein the linear array of detectors is comprised of a plurality of detector and extends parallel to the Y axis.

5. The arrangement according to claim 4, wherein approximately 512 of the detectors are provided.

6. The arrangement according to claim 2, wherein each detector element of the detector arrangement has a means for pulse height spectrum analysis.

7. The arrangement according to claim 2, wherein each detector element has a width in the Z direction of 0.5 mm to 2 mm and a length in the Y direction of 5 mm to 20 mm.

8. The arrangement according to claim 1, wherein the secondary ray collimator arrangement is comprised of several cylindrical collimator bodies surrounding one another and concentrically arranged relative to the axis of symmetry.

9. The arrangement according to claim 1, wherein the primary ray collimator arrangement is comprised of several lamellas of x-ray absorbing material, wherein the lamellas intercept one another in the Z axis and allow a ray divergence in the X-Y plane of 0.2 to 0.6°, have a length in the X direction between 100 and 300 mm, and a maximum angle in the X-Y plane from X axis of ±20°.

10. The arrangement according to claim 9, wherein the x-ray absorbing material is copper and wherein the ray divergence is 0.4°.

11. The arrangement according to claim 1, wherein the extended anode has a length in the Y direction of 1 m to 2 m, wherein across this length an electron beam is deflectable or the x-ray source has a plurality of 30 to 50 individual cathodes arranged adjacent to one another and switchable according to a sequence pattern, wherein the focal length of the anode is 30 to 60 mm in the Y direction and an effective focus width in the Z direction is 0.2 mm, and wherein the residence time for each switched focus position is 200 to 2000 µs.

12. The arrangement according to claim 11, wherein the extended anode has a length in the Y direction of 1.5 m.

13. The arrangement according to claim 1, wherein the anode is a solid anode comprised of tungsten or gold and is cooled with a cooling agent.

14. The arrangement according to claim 3, wherein the cooling agent is water or oil.

15. A method for inspecting containers with regard to explosives, weapons, and drugs, the method comprising the steps of:

provining a scanning area;

arranging a polychromatic x-ray source on one side of the scanning area and a detector arrangement on the other side of the scanning area;

arranging a primary ray collimator arrangement between the scanning area and the x-ray source and a secondary ray collimator arrangement, allowing passage only of scattered rays within a certain scatter angle range to the detector arrangement, between the scanning area and the detector arrangement;

positioning the detector arrangement on a Z axis, which simultaneously forms an axis of symmetry about which the secondary ray collimator arrangement extends cylindrically symmetrically;

providing a point 0 on the Z axis which determines the origin of a Cartesian coordinate system with X axis and Y axis;

wherein the x-ray source is arranged behind the primary ray collimator arrangement together with an extended anode having a focus position;

wherein the primary ray collimator arrangement allows passage only of x-ray beams which are substantially impinging on the point 0;

positioning the primary ray collimator arrangement and the x-ray source cylindrically symmetrically about the axis of symmetry or linearly parallel to the Y axis in the X-Y plane;

conveying a container to be examined parallel to the Z axis into the scanning area;

emitting x-ray radiation from the x-ray source onto the container and controlling electronically the focus position of the anode about the length of the anode;

measuring the energy of the scattered x-ray quanta scattered on the container with the detector arrangement and processing the output signals of the detector arrangement to generate radiographic images.

* * * * *